United States Patent [19]

Miserlis

[11] 4,435,581

[45] Mar. 6, 1984

[54] PROCESS FOR THE PRODUCTION OF PHTHALIC ANHYDRIDE

[75] Inventor: Constantine D. Miserlis, Arlington, Mass.

[73] Assignee: The Badger Company, Inc., Cambridge, Mass.

[21] Appl. No.: 374,385

[22] Filed: May 3, 1982

[51] Int. Cl.$^3$ .......................................... C07D 307/89
[52] U.S. Cl. .................................... 549/248; 549/249; 549/250; 549/256; 549/257; 549/258
[58] Field of Search ............... 549/248, 249, 250, 256, 549/257, 258

[56] References Cited

U.S. PATENT DOCUMENTS 4,215,053 7/1980 Palmer ................................. 549/248

*Primary Examiner*—Richard Raymond
*Attorney, Agent, or Firm*—Schiller & Pandiscio

[57] ABSTRACT

A system for producing phthalic anhydride by the catalytic oxidation of naphthalene, wherein the system is characterized by reduced capital and operating costs due to lower operating pressures.

18 Claims, 2 Drawing Figures

PROCESS FOR THE PRODUCTION OF PHTHALIC ANHYDRIDE

FIELD OF THE INVENTION

This invention relates to the production of carboxylic acids, dicarboxylic acids or their anhydrides by catalytic oxidation of aromatic or unsaturated aliphatic hydrocarbons.

BACKGROUND OF THE INVENTION

It is well known in the art that carboxylic acids, dicarboxylic acids or their anhydrides may be produced by catalytic oxidation of aromatic hydrocarbons such as benzene, o-xylene or naphthalene, or of unsaturated aliphatic hydrocarbons such as butadiene, n-butene or mixtures containing butadiene and/or n-butene. In such catalytic oxidation, which has achieved industrial importance particularly for the production of phthalic anhydride, the hydrocarbon is reacted with an oxygen-bearing gas in a reactor, under appropriate temperature and pressure conditions and in the presence of one or more suitable catalysts. The desired acid or acid anhydride produced by the reaction is contained in the reactor effluent and is subsequently separated out and recovered.

Figure 1:
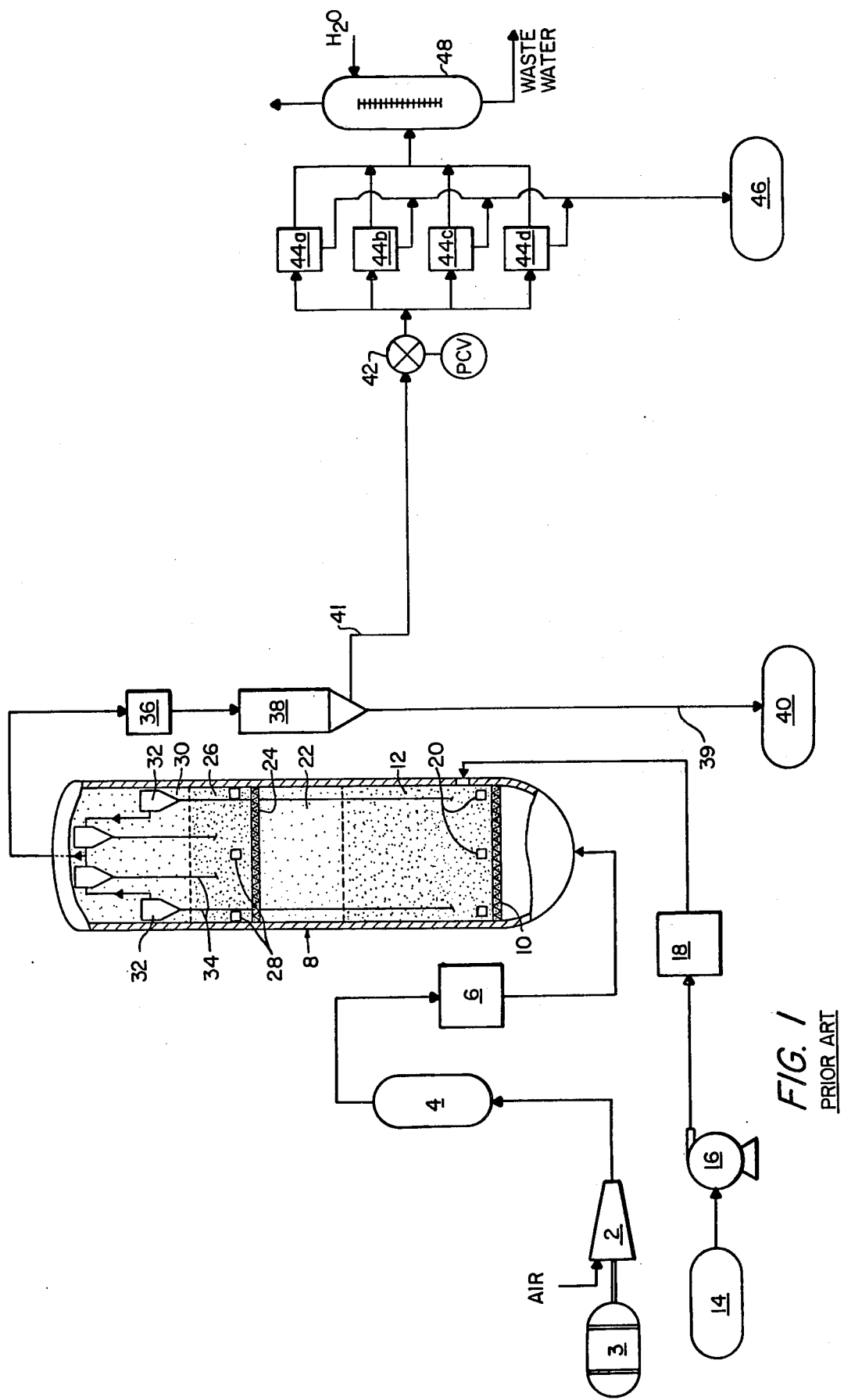
FIG. 1 is a process flow sheet showing a widely used prior art system for producing phthalic anhydride from catalytic oxidation of naphthalene.

FIG. 1 shows in more detail a conventional system for producing phthalic anhydride by the catalytic oxidation of naphthalene. Oxygen-bearing air is compressed by a compressor 2 driven by a motor 3 and is sent to an air receiver 4. A stream of air from air receiver 4 is heated to about 300° F. in an air heater 6 and then enters the bottom of a reactor 8. This air passes into a vanadium pentoxide-bearing catalyst bed 12 which is disposed on grid 10. The air entering the bottom end of the reactor is pressurized to about 37 psig.

At the same time, molten naphthalene is pumped from a storage tank 14 by a metering pump 16 through a vaporizer 18 where the naphthalene is vaporized before being injected into catalyst bed 12. Bed 12 is fluidized by the air and the naphthalene, and the primary oxygen/naphthalene reaction takes place in contact with catalyst bed 12. The rate at which the molten naphthalene is introduced into bed 12 is coordinated with the rate at which the oxygen-bearing air is introduced into bed 12 so that the reactor's catalyst bed 12 receives air and napthalene in a ratio of about 10:1 by weight. Bed 12 is maintained at a reaction temperature of between about 600° F. and about 750° F. by means of suitable temperature control elements represented schematically at 20.

Reacted gases flow up out of the top of fluidized catalyst bed 12 to a disengagement zone 22 where entrained catalyst particles will tend to disengage from the gases and settle back down onto bed 12. The reacted gases continue to rise and pass into a vanadium pentoxide-bearing catalyst bed 26 which resides on grid 24. Bed 26 is in turn fluidized by these gases. Catalyst bed 26 serves as a quench bed for the reacted gases, and to this end bed 26 is maintained at a selected quench temperature of about 525° F. by means of temperature control elements represented schematically at 28. The latter, like temperature control elements 20, may be individually controlled U-shaped tubular heat exchangers carrying a suitable heat exchange fluid. The quenched gases thereafter pass from fluidized catalyst bed 26 to a disengagement zone 30 where catalyst particles which may have been carried from bed 26 by the rising gases will tend to disengage from the gases and settle back down into bed 26.

A plurality f cyclones 32 are positioned at the top end of disengagement zone 30 and serve to purge the reacted gases of any lingering catalyst particles before the gaseous effluent leaves the reactor and is processed to recover desired components. Each cyclone is provided with a dip-leg 34 for returning the separated catalyst fines back to catalyst beds 12 and 26.

The gas stream leaving cyclones 32 is passed through a gas cooler 36 where the stream is cooled to a temperature just above the dew point of phthalic anhydride, i.e. approximately 315° F. The cooled stream then passes into a partial condenser 38 where up to approximately one-half of the phthalic anhydride that is present in the gaseous stream is condensed out as a liquid. The liquid phthalic anhydride is separated from the remaining gas stream and it flows via a line 39 to a liquid storage tank 40 for subsequent processing.

The gas stream exiting partial condenser 38 has a temperature of approximately 300° F. It passes via a line 41 and a pressure control valve 42 to one of a battery of switch condensers 44a, 44b, 44c, etc. Switch condensers 44a, 44b, 44c, etc. serve to remove the phthalic anhydride remaining in the effluent stream by sublimating the phthalic anhydride out of the reactor effluent as a solid. When a given switch condenser has condensed out a predetermined amount of phthalic anhydride, the switch condenser is shut off from the incoming gas stream and is switched over to a heating cycle to melt the condensed phthalic anhydride. Simultaneously, another switch condenser, which at this point has been re-cooled after completing its heating cycle, is opened to the gas stream to condense incoming phthalic anhydride. The phthalic anhydride which is melted in any of the switch condensers is directed to a liquid storage tank 46 for further processing. The effluent gas stream that leaves a cooling switch condenser is sent to a gas scrubber 48 where it is washed with water before being vented to the atmosphere or to other process equipment for further treatment or recovery. The gas stream preferably leaves the switch condensers at a temperature of between about 125° F. and about 140° F. before being directed to the scrubber 48.

Pressure control valve 42, disposed in the gas line intermediate partial condenser 38 and switch condensers 44a, 44b, 44c, etc., imposes a back pressure on reactor 8 which is necessary in the practice of the production system. By controlling the gas pressure at this point in the process the phthalic anhydride can be condensed in partial condenser 38 as a liquid instead of as a solid. This is so, because increased pressure can raise the dew point of phthalic anhydride above the melting point, thereby permitting condensation of the phthalic anhydride directly as a liquid. In the system described above, the pressure control valve is designed to hold the reactor top pressure at about 22 psig.

Unfortunately, a number of difficulties arise when a process of the sort just described is utilized.

First, it has been found that the cyclones 32 are incapable of removing all of the catalyst dust from the reaction gases before the gases leave the reactor. As a result, small amounts of catalyst dust (typically between about 0.007% and about 1.0% by weight) leave the reactor with the effluent and travel on to the downstream process elements. The dust tends to remain in the gaseous effluent as it passes through gas cooler 36, partial condenser 38 and pressure control valve 42 and enters switch condensers 44a, 44b, 44c, etc. Inside the switch condensers, the catalyst dust in the reactor effluent creates complications when the condensers switch to their cooling cycle to sublimate out phthalic anhydride from the gas as a solid. In particular, the dust particles serve as growth nuclei for condensing phthalic anhydride and enable some of the phthalic anhydride to condense out of the effluent as a gas-born mist rather than sublimating substantially entirely as a solid deposited directly on the surfaces of the switch condensers. Unfortunately the phthalic anhydride mist tends to deposit and solidify on the switch condenser surfaces as a dense, slushy mass which is relatively unporous and which has a relatively poor heat transfer coefficient, whereas sublimated phthalic anhydride deposits on the switch condenser surfaces as a group of needle-like crystals which are relatively porous and which have a relatively good heat transfer coefficient. The deposition of a dense, slushy mass is detrimental since it will not melt out as rapidly as the needle-like crystals. Hence, unless the time for melting out the phthalic anhydride is increased (at a consequent increase in heating costs), there will be a gradual buildup of phthalic anhydride which will cause an undesirable back pressure buildup. The back pressure increases in the switch condensers may necessitate the use of a bigger and more expensive compressor 2 and a bigger and more expensive motor 3 to make the production system operate. In addition, the formation of slushy dense phthalic anhydride due to the presence of significant quantities of catalyst dust in the switch condensers is of concern because it may necessitate increasing the time allotted for (a) cooling the effluent stream to the temperature required to condense out the phthalic anhydride, and (b) melting out deposited phthalic anhydride in a full switch condenser.

A second problem encountered with the phthalic anhydride production system shown in FIG. 1 is one of cost. The production system shown requires the use of a compressor 2 and a motor 3 which are capable of delivering significant quantities of air to reactor 8 at a pressure of about 37 psig. For a typical plant capable of producing about 10,000 metric tons of phthalic anhydride per year, this means a compressor and motor installation rated at about 1100 horsepower and costing about $750,000. This is a significant portion of the total capital cost of the entire system. In addition, the energy costs involved in operating the motor are quite large. For example, with the typical plant just described the annual power costs for the motor, calculated at an energy cost of 6¢ per kwh, is about $400,000 per year. In this respect it is to be appreciated that the power requirements of the motor comprise the principal power requirements of the entire production system.

Prior to this invention, applicant solved the first of these problems, i.e., the catalyst dust problem, by inserting a venturi scrubber stage into line 41 between partial condenser 38 and pressure control valve 42. This added stage serves to scrub substantially all of the catalyst dust out of the reactor effluent before the effluent reaches the switch condensers. As a result, the phthalic anhydride is recovered in the switch condensers as a sublimated solid instead of as a troublesome sludge.

Unfortunately, while the incorporation of the scrubber stage into the phthalic anhydride production system substantially solves the catalyst dust problem, it does not solve the second of the aforementioned problems, the cost problem.

OBJECTS OF THE PRESENT INVENTION

As a result, the principle object of the present invention is to provide a phthalic anhydride production system which is cheaper to construct and operate than a phthalic anhydride production system of the type shown in FIG. 1.

SUMMARY OF THE INVENTION

These and other objects of the present invention are achieved by providing a phthalic anhydride production system which differs from the production system shown in FIG. 1 in several respects. A simple blower arrangement is used to deliver air to a reactor at a relatively low pressure. Naphthalene is introduced separately into the reactor. The air and naphthalene mix in the reactor in a catalyst bed at the appropriate reaction temperature so as to produce a gaseous reactor effluent which comprises gaseous phthalic anhydride. The reactor effluent passes out of the top end of the reactor and through a gas cooler where it is cooled significantly from its relatively high reaction temperature. Then the effluent is passed through a plurality of cyclones so that most of the catalyst dust entrained in the effluent is purged from the effluent. The gas stream leaving the cyclones is next passed through a desuperheater where the effluent is cooled to a temperature below the autoignition temperature of the phthalic anhydride contained in the effluent. Then the effluent is passed through a venturi scrubber stage where the effluent is purged of any remaining catalyst particles. The effluent leaving the venturi scrubber stage is next passed through a battery of switch condensers where the phthalic anhydride contained in the effluent is sublimated out and recovered. The effluent leaing the switch condensers is directed on to various pollution control equipment for processing.

Other objects and features of the present invention are specified or made obvious by the following detailed description of a preferred embodiment of the invention.

DETAILED DESCRIPTION OF THE PREFERRED EMBODIMENT

Figure 2:
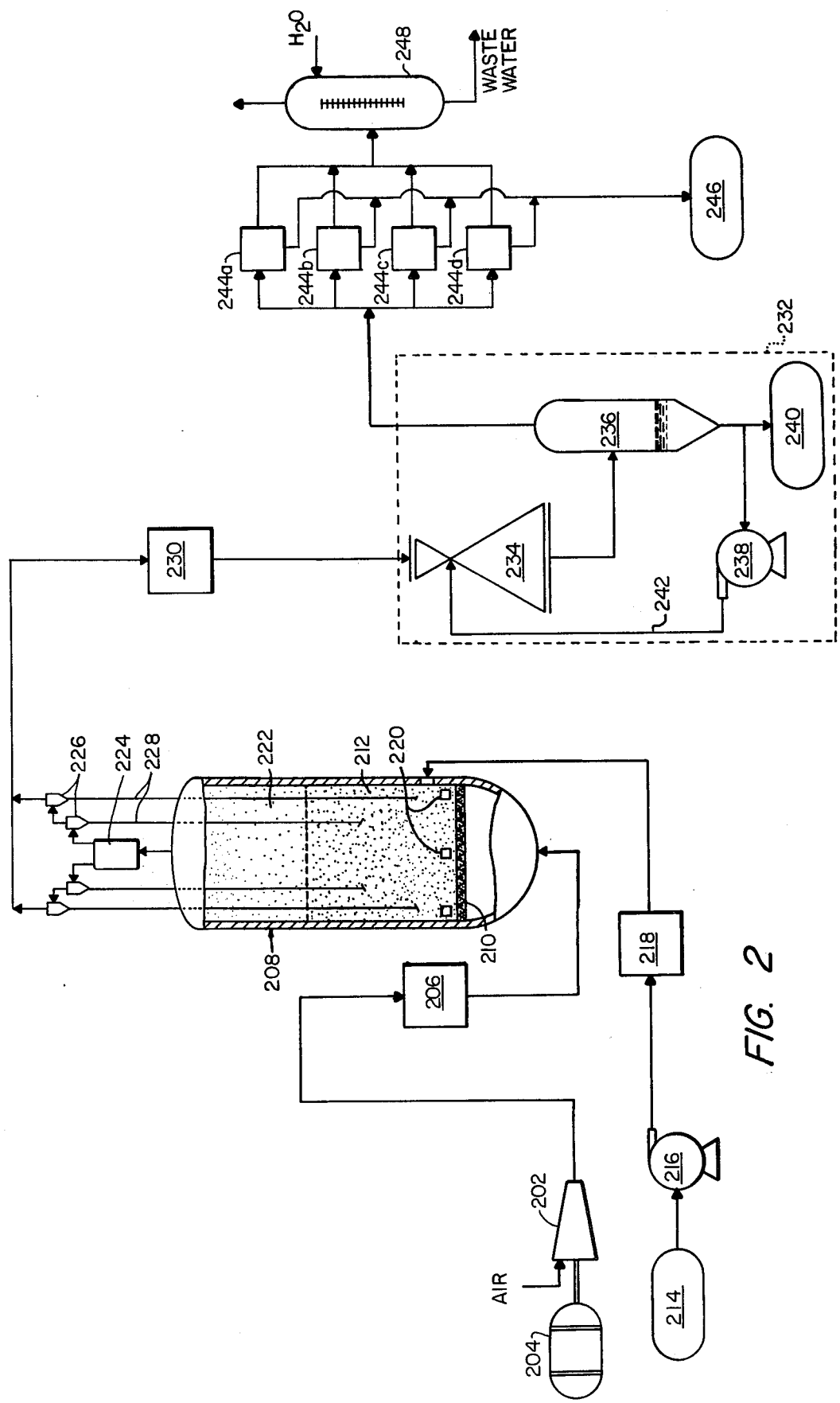
FIG. 2 is a process flow sheet showing a system constituting the preferred form of the invention for producing phthalic anhydride by catalytic oxidation of naphthalene.

Referring now to FIG. 2, oxygen-bearing air enters the intake port of an air blower 202 powered by a motor 204 and is sent through an air heater 206 before it enters the bottom end of a reactor 208. This air passes through a grid 210 into a vanadium pentoxide-bearing catalyst bed 212 which is disposed on grid 210. The air entering reactor 208 as a temperature of about 300° F. and is pressurized to about 12.5 psig.

At the same time, molten naphthalene is pumped from a storage tank 214 by a metering pump 216 through a vaporizer 218 where the naphthalene is vaporized before being injected into catalyst bed 212. Bed 212 is fluidized by the air and the naphthalene, and the primary oxygen/naphthalene reaction takes place in contact with catalyst bed 212. The rate at which the molten naphthalene is introduced into bed 212 is coordinated with the rate at which the oxygen-bearing air is introduced into bed 212 so that the reactor's catalyst bed 212 receives air and naphthalene in a ratio of about 10:1 by weight. Bed 212 is maintained at a reaction temperature of between about 600° F. and about 750° F. by means of suitable temperature control elements 220.

Reacted gases flow upward out of the top of fluidized catalyst bed 212 to a disengagement zone 222 where catalyst particles which may have been carried upward from bed 212 by the rising gases will tend to disengage from the gases and settle back down onto bed 212.

The reacted gases continue to rise and pass out of the top end of reactor 208 and into a gas cooler 224. The reacted gases enter cooler 224 with a pressure of about 5 psig. Gas cooler 224 is a shell and tube gas cooler of conventional design. Circulating water is used as the cooling medium in cooler 224. Cooler 224 serves to cool the gas stream exiting the reactor from its reaction temperature of between about 600° F. and about 750° F. to a temperature of about 500° F. After being cooled by gas cooler 224, the reactor effluent is passed through a plurality of cyclones 226 where most of the catalyst particles still lingering in the effluent are removed. Each cyclone 226 is provided with a dip-leg 228 for returning the separated catalyst fines back to catalyst bed 212.

The gas stream leaving cyclones 226 is next passed through a water-cooled desuperheater 230 where the stream is cooled still further to a selected temperature, preferably about 315° F., which is well below the 385° F. autoignition temperature of the phthalic anhydride contained in the gas stream, but about 5° above the dew point of the phthalic anhydride in the stream. As a result of this cooling, the gas stream can be passed safely through a venturi scrubber stage hereinafter described without fear that the phthalic anhydride in the gas stream will autoignite as it passes through the stage.

Upon leaving desuperheater 230 the reactor effluent is passed through a venturi scrubber stage 232. Stage 232 serves to remove any lingering catalyst particles which may still be entrained in the effluent. Venturi scrubber stage 232 comprises a venturi 234, a separator vessel 236, a recycle pump 238, and a storage tank 240. Pump 238 is disposed in a line 242 connecting a drawoff port of separator 236 to venturi 234. The drawoff port of vessel 236 is also connected to tank 240, while the overhead port of vessel 236 is connected to a battery of switch condensers 244a, 244b, 244c, etc. as hereinafter described in further detail.

In scrubber stage 232 the gaseous effluent stream passes into the entrance of venturi 234, where it comes into contact with a liquid scrubbing stream of molten phthalic anhydride which is injected into the throat of venturi 234 via line 242. As a consequence of such contact, the catalyst particles are scrubbed out of the effluent and entrained in the liquid phthalic anhydride. Thereafter, the molten phthalic anhydride (bearing the catalyst particles) and the reactor effluent (devoid of catalyst particles) pass to separator 236 where they are separated, with the molten phthalic anhydride being withdrawn for recycling back to venturi 234, and the gaseous effluent being withdrawn for delivery to the battery of switch condensers 244a, 244b, 244c, etc. The catalyst dust which entered venturi 234 entrained in the reactor effluent is entrapped in the phthalic anhydride and recovered in the separator, so that the effluent which passes from separator 236 to the switch condensers is substantially dust free. The reactor effluent leaving separator 236 has a pressure of about 2 to 3 psig.

In order to prevent the level of catalyst particles in the phthalic anhydride scrubbing stream from building up to the point where it might interfere with the scrubbing operation, part of the phthalic anhydride withdrawn from separator 236 is continually purged away to storage tank 240. This purged phthalic anhydride can then be refined to remove suspended catalyst particles and the refined phthalic anhydride can be recovered as product.

The molten phthalic anhydride recirculated in line 242 of the scrubbing apparatus is kept at about 290° F. so that its temperature is very near to that of the effluent entering the venturi. This close temperature proximity between the scrubbing liquid and the effluent is desired to ensure that there is no rapid shock cooling of the effluent at the venturi which might inhibit the efficiency of the scrubbing operation.

Switch condensers 244a, 244b, 244c, etc. serve to remove the phthalic anhydride contained in the catalyst-free gaseous effluent received from separator 236 by sublimating the phthalic anhydride as a solid which deposits on the surfaces of the switch condensers as a mass of needle-like crystals having a relatively good heat transfer coefficient. The phthalic anhydride which is captured by the switch condensers is subsequently melted and collected in storage tank 246 for further processing. The effluent stream that leaves the switch condensers is sent to a gas scrubber 248 where it is washed with water before being vented to the atmosphere or to other process equipment for further treatment or recovery.

EXAMPLE

A reactor as generally illustrated in FIG. 2 of the drawings, having a diameter of approximately 13 feet and a height of about 50 feet, is charged with about 10,000 pounds of a vanadium pentoxide-containing catalyst to form its bed 212. Air is fed into the bottom of the reactor at about 5790 standard cubic feet per minute, at a pressure of about 12.5 psig and a temperature of about 300° F. Naphthalene vapor is metered into the catalyst bed 212 at a rate of about 135 standard cubic feet per minute, at a pressure of about 15 psig and a temperature of about 500° F. The air to naphthalene ratio entering the fluidized bed 212 is about 10:1 by weight. The gaseous mixture of air, naphthalene and reaction products passes upwardly at a superficial velocity of about 1 to 1.5 feet per second, fluidizing the catalyst particles in bed 212 so that the bed has a height of about 25 feet. The average pressure in the fluidized bed is about 10 pounds per square inch gauge. The reaction temperature of fluidized bed 212 is maintained at about 675° F., which is the temperature which produces the maximum yield of phthalic anhydride.

The gases passing out of bed 212 pass through a disengagement zone 222 which is approximately 25 feet in height, and then enter gas cooler 224. Cooler 224 cools the reactor effluent to a temperature of about 500° F. The effluent entering gas cooler 224 has a pressure of about 5 psig.

Next the gases are passed through cyclones 226 for removal of catalyst particles. The gas stream leaves cyclones 226 at a temperature of about 475° F. and passes on to a desuperheater 230 where the stream is cooled to a temperature of about 315° F.

The gas stream leaving desuperheater 230 enters venturi 234 at a temperature of about 315° F. and a pressure of about 3.5 psig, and meets a stream of molten phthalic anhydride which is injected into the throat of the venturi at a temperature of about 290° F. and a pressure of about 3.0 psig. The molten phthalic anhydride scrubs the catalyst particles from the effluent. The dust-laden molten phthalic anhydride and the gas stream are separated in separator 236 with the gases passing to the switch condensers 244a, 244b, 244c, etc., and the molten phthalic anhydride passing partly to drawoff tank 240 and partly through recycle line 242 back to venturi 234. About 80 to 90% of the phthalic anhydride removed from separator 236 is recycled to venturi 234. The gas stream leaving separator 236 is directed into selected ones of the switch condensers for sublimation depositions. The gas stream enters the selected switch condenser(s) at a pressure of about 2.5 psig and a temperature of about 290° F. The switch condensers are operated so as to sublimate out phthalic anhydride at a rate of about 99.5% of the amount present in the entering gas stream. The gases exiting the switch condensers have a temperature of about 125° F. Each switch condenser is switched out of the system after about 4 to 6 hours of operation, and substantially all (98%+) of the phthalic anhydride in the condenser is recovered in about 0.75 to one hours by heating the condenser to a temperature of about 375° F. to 400° F. and maintaining it at that temperature until recovery is completed.

The concentrations of catalyst dust in the gaseous effluent entering venturi 234 is about 0.01%. As a consequence of the dust removal effected by scrubber stage 232, the catalyst concentration in the effluent entering the switch condensers is reduced to less than 10 ppm. Because of the reduction in catalyst dust concentration, the system is able to recover over 99.5% of all the phthalic anhydride produced in fluidized catalytic reactor 208.

MODIFICATIONS OF THE PREFERRED EMBODIMENT

It is, of course, possible to modify the phthalic anhydride production system shown in FIG. 2 without departing from the scope of the present invention.

Thus, for example, the invention may be practiced with a fluid bed reactor having a plurality of fluid beds or a reactor which includes a quench bed as shown in FIG. 1. Alternatively, the invention may be practiced with a fixed bed reactor.

It also is to be understood that the invention may be practiced with different operating conditions, i.e., the temperatures, pressures and flow rates may be altered without affecting the improvements resulting from this invention. Thus, for example, the air may enter the reaction vessel at ambient temperature and undergo heating entirely within the reactor itself, or the naphthalene may be fed into the reactor as a liquid and be vaporized upon contact with catalyst bed 212, or be injected into the reactor below grid 210 as a vapor.

The system may be modified in other obvious ways. For example, the number and type of switch condensers may be varied.

The system shown in FIG. 2 also may be adapted to produce phthalic anhydride by the oxidation of ortho-xylene. In such a case, it might be necessary to use special promoters (as described in U.S. Pat. No. 3,407,215) or a special catalyst (as described in British Pat. No. 1192416) to support the reaction within the reactor.

The present invention also may be used to prepare carboxylic acids, dicarboxylic acids, or their anhydrides (other than phthalic anhydride) by the catalytic oxidation of aromatic hydrocarbons such as benzene, ortho-xylene or naphthalene, or of unsaturated aliphatic hydrocarbons such as butadiene, n-butene or mixtures containing butadiene and/or n-butene. These and other possible changes of similar type are obvious to those skilled in the art and hence are to be considered within the scope of the present invention.

ADVANTAGES OF THE INVENTION

Several advantages are obtained by using the present invention.

First, by employing the phthalic anhydride production system shown in FIG. 2 instead of the phthalic anhydride production system shown in FIG. 1, there is a substantial economic advantage. Whereas the system shown in FIG. 1 requires a compressor and motor installation capable of delivering air to the reactor at a pressure of about 37 psig, the system shown in FIG. 2 can operate with a blower and motor installation delivering air to the reactor at a pressure of only about 12.5 psig. This translates into significant savings in capital and operating costs. For example, in a typical plant capable of producing about 10,000 metric tons of phthalic anhydride per year, the production system of FIG. 1 would require a compressor and motor installation rated at about 1100 horsepower and costing about $750,000, whereas the production system of FIG. 2 would require a blower and motor installation rated at about 500 horsepower and costing about $57,000. In addition, the power costs for running the motors vary considerably depending on the system: at an energy cost of 6¢ per kwh, it costs about $400,000 per year to run the motor used in the system of FIG. 1 whereas it costs only about $180,000 per year to run the motor used in the system of FIG. 2.

Another advantage of the present invention is that it may be practiced in systems which produce products other than phthalic anhydride, i.e., it can be utilized in systems producing carboxylic acids, dicarboxylic acids and their anhydrides (other than phthalic anhydride) by the catalytic oxidation of aromatic hydrocarbons such as benzene, ortho-xylene or naphthalene, or of unsaturated aliphatic hydrocarbons such as butadiene, n-butene, or mixtures of butadiene and/or n-butene.

Still other advantages will be obvious to persons skilled in the art.

What I claim is:

1. A process for producing an anhydride of a carboxylic or dicarboxylic acid, said process comprising the steps of:
   (a) reacting an aromatic hydrocarbon or an unsaturated aliphatic hydrocarbon with oxygen in a reactor in the presence of a catalyst under selected conditions so as to produce a gas stream which comprises an anhydride of a carboxylic or dicarboxylic acid;
   (b) passing said gas stream from said reactor to a gas cooler where said gas stream is cooled to a temperature above the auto-ignition temperature of said anhydride;
   (c) passing said gas stream from said gas cooler to at least one cyclone in order that said at least one cyclone may purge catalyst particles from said gas stream;

(d) passing said gas stream from said at least one cyclone to a temperature which is below the autoignition temperature of said anhydride yet is above the dew point of said anhydride;

(e) passing said gas stream from said desuperheater to a venturi scrubber stage and scrubbing said gas stream so as to purge it of substantially all entrained catalyst dust particles;

(f) passing said gas stream from said scrubber stage to at least one switch condenser;

(g) sublimating substantially all of said anhydride out of said gas stream so as to cause said anhydride to deposit as a solid in said at least one condenser; and (h) recovering said solid from said at least one condenser.

2. A process according to claim 1 wherein said scrubber stage comprises a venturi and a separator, and further wherein said gas stream passes from said desuperheater into said venturi in contact with recycled liquid anhydride and the mixture of said gas stream and liquid anhydride is passed from said venturi into said separator where said liquid anhydride and said entrained dust particles are separated from said gas stream, whereby said gas stream is substantially free of dust particles as it passes to said at least one switch condenser.

3. A process according to claim 2 wherein at least some of the liquid anhydride separated from said gas stream in said separator is purged.

4. A process according to claim 2 wherein at least some of the anhydride separated from said gas stream is recycled to said scrubber and the remainder of said liquid anhydride is recovered from the scrubber stage so as to limit the buildup of catalyst dust particles in the liquid anhydride recycled to the venturi.

5. A process according to claim 4 wherein said liquid anhydride circulating in said scrubber stage is maintained at a temperature close to the temperature of said gas stream as it enters said scrubber stage, in order that said gas stream will not undergo rapid shock cooling when it is contacted with said liquid anhydride in said scrubber stage.

6. A process according to claim 5 wherein said gas stream enters said venturi scrubber stage at a temperature of about 315° F., and said liquid phthalic anhydride is heated to a temperature of about 290° F.

7. A process according to claim 5 wherein said catalyst is fluidized in said reactor.

8. A process according to claim 5 wherein said oxygen is delivered to said reactor at a pressure of about 12.5 psig, and further wherein said gas stream exits said reactor at a pressure of about 5 psig and enters said at least one switch condenser at a pressure of about 3 1 psig.

9. A process according to claim 8 wherein said gas stream leaves said reactor at a temperature of between about 600° F. and 750° F., and further wherein said gas stream leaves said gas cooler at a temperature of about 500° F.

10. A process according to claim 9 wherein said gas stream is cooled in said desuperheater to a temperature of about 315° F.

11. A process for producing phthalic anhydride comprising the steps of:

(a) oxidizing naphthalene or o-xylene in a reactor in the presence of a catalyst under selected conditions to produce a gas stream which comprises phthalic anhydride;

(b) passing said gas stream from said reactor to a gas cooler where said gas stream is cooled to a temperature above the autoignition temperature of said phthalic anhydride;

(c) passing said gas stream from said gas cooler to at least one cyclone in order that said at least one cyclone may purge catalyst particles from said gas stream;

(d) passing said gas stream from said at least one cyclone to a desuperheater where said gas stream is cooled to a temperature which is (1) below the autoignition temperature of said phthalic anhydride and (2) above the dew point of said phthalic anhydride;

(e) passing said gas stream from said desuperheater to a venturi scrubber stage and scrubbing said gas stream so as to purge it of substantially all entrained catalyst dust particles;

(f) passing said gas stream from said scrubber stage to at least one switch condenser;

(g) sublimating substantially all of said phthalic anhydride out of said gas stream so as to cause said phthalic anhydride to deposit as a solid in said at least one condenser; and (h) recovering said solid from said at least one condenser.

12. A process according to claim 11 wherein said scrubber stage comprises a venturi and a separator, and further wherein said said gas stream passes from said desuperheater into said venturi in contact with recycled liquid phthalic anhydride and the mixture of said gas stream and liquid phthalic anhydride is passed from said venturi into said separator where said liquid phthalic anhydride and said entrained dust particles are separated from said gas stream, whereby said gas stream is substantially free of dust particles as it passes to said at least one switch condenser.

13. A process according to claim 12 wherein at least some of the liquid phthalic anhydride separated from said gas stream in said separator is purged.

14. A process according to claim 12 wherein at least some of the phthalic anhydride separated from said gas stream is recycled to said scrubber and the remainder of said liquid phthalic anhydride is recovered from the scrubber stage so as to limit the buildup of catalyst dust particles in the liquid phthalic anhydride recycled to the venturi.

15. A process according to claim 14 wherein said liquid phthalic anhydride circulating in said scrubber stage is maintained at a temperature close to the temperature of said gas stream as it enters said scrubber stage, in order that said gas stream will not undergo rapid shock cooling when it is contacted with said liquid acid or anhydride in said scrubber stage.

16. A process according to claim 11 wherein said catalyst comprises vanadium pentoxide.

17. A process according to claim 16 wherein said catalyst is fluidized in said reactor.

18. A process according to claim 11 wherein said oxygen is delivered to said reactor at a pressure of about 12.5 psig, and further wherein said gas stream exits said reactor at a pressure of about 5 psig and enters said at least one switch condenser at a pressure of about 3 psig.

* * * * *

UNITED STATES PATENT AND TRADEMARK OFFICE
CERTIFICATE OF CORRECTION

PATENT NO. : 4435581
DATED : March 6, 1984
INVENTOR(S) : Constantine D. Miserlis It is certified that error appears in the above-identified patent and that said Letters Patent is hereby corrected as shown below:

Claim 8, column 9, line 54, the mark resembling the number 1 immediately after the number "3", should be deleted.

Claim 12, column 10, line 32, the word "said" (second occurrence), should be deleted.

Signed and Sealed this

Twenty-ninth Day of May 1984

[SEAL]

Attest:

GERALD J. MOSSINGHOFF

Attesting Officer    Commissioner of Patents and Trademarks